US011865353B2

(12) United States Patent
Milpied et al.

(10) Patent No.: US 11,865,353 B2
(45) Date of Patent: *Jan. 9, 2024

(54) ACTIVE IMPLANTABLE MEDICAL DEVICE FOR DETECTING AND QUANTIFYING FUSION

(71) Applicant: SORIN CRM SAS, Clamart (FR)

(72) Inventors: Paola Milpied, Paris (FR); Delphine Feuerstein, Issy-les-Moulineaux (FR)

(73) Assignee: SORIN CRM SAS, Clamart (FR)

( * ) Notice: Subject to any disclaimer, the term of this patent is extended or adjusted under 35 U.S.C. 154(b) by 168 days.

This patent is subject to a terminal disclaimer.

(21) Appl. No.: 17/176,072

(22) Filed: Feb. 15, 2021

(65) Prior Publication Data

US 2021/0308474 A1    Oct. 7, 2021

Related U.S. Application Data

(63) Continuation of application No. 15/344,361, filed on Nov. 4, 2016, now Pat. No. 10,918,876.

(30) Foreign Application Priority Data

Nov. 5, 2015    (FR) ...................... 1560620

(51) Int. Cl.
*A61N 1/39*    (2006.01)
*A61N 1/368*    (2006.01)
*A61N 1/37*    (2006.01)
*A61B 5/316*    (2021.01)

(52) U.S. Cl.
CPC ............ *A61N 1/3956* (2013.01); *A61B 5/316* (2021.01); *A61N 1/3682* (2013.01); *A61N 1/37* (2013.01); *A61N 1/371* (2013.01); *A61N 1/3925* (2013.01)

(58) Field of Classification Search
CPC .............. A61N 1/3684; A61N 1/36842; A61N 1/36843; A61N 1/0563; A61N 1/365;
(Continued)

(56) References Cited

U.S. PATENT DOCUMENTS 10,918,876 B2 *  2/2021  Milpied ............... A61N 1/3682
2008/0119903 A1    5/2008  Arcot-Krishnamurthy et al.
(Continued)

FOREIGN PATENT DOCUMENTS

EP    2 324 885 A1    5/2011
EP    2368493 A1    9/2011
(Continued)

OTHER PUBLICATIONS

Milpied et al., "Implantable Cardioverter Arrhythmia Discrimination in Defibrillators using Support Vector Machines Applied to a New Representation of Electrograms," IEEE Transactions on Biomedical Engineering, Jun. 2011, 58 (6): 1797-1803.
(Continued)

*Primary Examiner* — Jon Eric C Morales

(57) ABSTRACT

Disclosed are systems, devices and methods that produce at least two distinct temporal components from two distinct endocardial electrogram (EGM) signals collected concurrently, determines a non-temporal 2D characteristic representative of the cardiac cycle to be analyzed, from the variations of one of the temporal components as a function of another of the temporal components and comparing the characteristic of the current cycle to two reference characteristics previously obtained and stored, one in a situation of complete capture and the other in a situation of spontaneous rhythm. Respective values of similarity descriptors are derived of these two comparisons, which are used to calculate a metric quantifying a fusion rate.

20 Claims, 7 Drawing Sheets

(58) Field of Classification Search
CPC ...... A61N 1/3682; A61N 1/371; A61N 1/056;
A61N 1/3627; A61N 1/3702; A61N
1/3925; A61N 1/39622; A61B 5/283;
A61B 5/287; A61B 5/316; A61B 5/318;
A61B 5/341; A61B 5/349; A61B 5/361;
A61B 5/686; A61B 5/7246; A61B
5/7275; A61B 5/746

See application file for complete search history.

(56) References Cited

U.S. PATENT DOCUMENTS

| | | |
|---|---|---|
| 2011/0118804 A1 | 5/2011 | Henry et al. |
| 2012/0310297 A1 | 12/2012 | Sweeney |
| 2014/0172037 A1 | 6/2014 | Euzen et al. |
| 2016/0303372 A1 | 10/2016 | Milpied et al. |

FOREIGN PATENT DOCUMENTS

| | | |
|---|---|---|
| EP | 2742971 A1 | 6/2014 |
| EP | 2742973 A1 | 6/2014 |
| EP | 2 756 865 A1 | 7/2014 |
| EP | 2873436 A1 | 5/2015 |

OTHER PUBLICATIONS

Preliminary Search Report for French Patent Application No. 1560620, dated Sep. 15, 2016, 2 pages.

\* cited by examiner

ACTIVE IMPLANTABLE MEDICAL DEVICE FOR DETECTING AND QUANTIFYING FUSION

CROSS-REFERENCE TO RELATED PATENT APPLICATIONS

This application is a continuation of U.S. application Ser. No. 15/344,361, filed Nov. 4, 2016, which claims the benefit of and priority to French Patent Application No. 1560620, filed Nov. 5, 2015, all of which are incorporated herein by reference in their entireties.

BACKGROUND

The present disclosure relates to "active implantable medical devices" as defined by Directive 90/385/EEC of 20 Jun. 1990 of the Council of the European Communities, specifically to implantable devices that continuously monitor heart rhythm and deliver to the heart, if necessary, stimulation, resynchronization and/or defibrillation pulses in the event of a rhythm disorder detected by the device.

The disclosure more particularly relates to a situation referred to as "fusion," that is to say an occurrence of a stimulation applied more or less concurrently with a spontaneous depolarization, naturally produced by the sinus node (in the case of atrial fusion) and/or the atrioventricular node (in the case of ventricular fusion).

In the context of the present disclosure, the term "intrinsic rhythm" will be understood as a spontaneous depolarization in the ventricles via the natural conduction pathways (His bundle, Purkinje fibers, etc.), regardless of the origin (stimulated or spontaneous) of depolarization in the atria.

The situation can arise in the context of a test called a "capture test" which, after stimulation of a cavity, detects, in this cavity, a presence or absence of an "evoked wave", that is to say a depolarization wave induced by the stimulation, in order to determine if the stimulation was effective or not. This test is particularly used for periodically changing the amplitude or width of the pulses applied to the stimulation site in order to adapt the energy delivered according to the efficacy threshold or "triggering threshold" of this site, so that the energy is sufficient to definitely induce an evoked wave, but not excessive, so as to not compromise the lifespan of the device.

If a fusion occurs during this test, that is to say, if stimulation is applied when a spontaneous QRS event occurs, the test algorithm will detect this situation because the evoked wave morphology will be different. In fact, the device may be able to detect a situation of suspected fusion, to first invalidate the test and adapt stimulation parameters (e.g., shortening of the atrioventricular delay AVD or increase of the stimulation frequency) to overcome these errors to complete the capture threshold test.

In general, it is important to detect the presence of a fusion within a bradycardia pacing of a stimulation device operating in classic "dual chamber" mode, that is to say that the device monitors the ventricular activity after a spontaneous atrial event (P-wave) or stimulated atrial event (A pulse) and triggers a stimulation of the right ventricle (V pulse) if no spontaneous ventricular activity (R wave) has been detected at the end of a period called "atrioventricular delay" (AVD). In this context, the presence of a fusion may reflect a preserved spontaneous conduction, and therefore the non-necessity of stimulation. If stimulation is inhibited, for example, by lengthening the AVD in case of ventricular fusion, not only will there be no deleterious effects of the stimulation (which might otherwise cause desynchronization and lead to atrial fibrillation or worsening of heart failure in the long term), but also device autonomy is preserved by a decrease in activity of the pulse generator.

Another situation where it may be useful to detect a fusion situation is that of a resynchronization therapy, called "CRT" (Cardiac Resynchronization Therapy) or "BVP" (Bi-Ventricular Pacing), where the heart rate is continuously monitored and, if necessary, electrical pulses are delivered to the heart to cause joint contraction of the left and right ventricles to resynchronize them. CRT therapy optimizes the contraction/relaxation cycle with a direct benefit facilitating the work of the heart, particularly in heart failure conditions wherein the aim is to stabilize a cardiac remodeling phenomenon (that is, all the heart changes brought in response to a disease, which is usually associated with a worse prognosis), and even counter this phenomenon ("reverse remodeling"), to obtain a better prognosis for the patient.

CRT therapy can be implemented with stimulation of the left ventricle only when the native right atrioventricular conduction is preserved, reducing the need for an unnecessary and harmful stimulation of the right ventricle. One should then seek to promote a fusion of the left stimulation with the spontaneous conduction of the right ventricle. In the presence of a full capture, or if the stimulation causes depolarization too close to the full capture), the AVD will have to be extended to ensure the fusion and achieve the desired mechanical effect of resynchronization of both ventricles.

This particular case of CRT therapy with stimulation of the left ventricle alone is not limiting, the fact of promoting fusion in the context of a CRT therapy being also applicable to the multipoint and/or biventricular stimulation. The fusion can be observed on a surface electrocardiogram (ECG), preferably using a large number of derivations to see the smallest morphological changes in the activation waves in case of fusion. However, the detection of fusion by the ECG is generally qualitative and variable depending on the operator. In any case, an automatic determination of the fusion, with objective quantification means and establishing of a metric or scale (hereinafter "degree of fusion"), is necessary to improve ventricular resynchronization and therefore for optimal operation of implantable CRT devices.

EP 2324885 A1 (Sorin CRM) discloses a technique of classification of each cardiac cycle in i) cycles in entire capture, ii) cycles in fusion or iii) cycles with loss of capture.

This classification is performed by a comparison of the current cycle with a single stored reference, corresponding to a complete capture situation. To differentiate a fusion situation from a capture loss situation, the present disclosure proposes a method based on two-dimensional analysis of two endocardial electrogram (EGM) signals concurrently collected on two separate channels and from the same cavity, including the right ventricle.

The two different EGM pathways may be a unipolar signal (distant signal collected between the housing and a distal or a proximal electrode) and a bipolar signal (close signal collected between a distal electrode and a proximal electrode), respectively. The two-dimensional analysis is performed on a "cardiac loop" or "vectogram" (VGM), which is a representation in a two-dimensional space of one of the two signals with respect to the other, each heart beat or significant fraction of heart beat being represented by its vectogram defined in the plan thus defined.

The analysis method is to describe each VGM by the velocity vector at each point of the loop. The VGM produced for a particular stimulation energy is then compared to a reference VGM obtained at maximum energy.

To differentiate the fusion of the loss of capture, the algorithm is based on the values of the descriptor used for comparison: this descriptor is compared to a first threshold for deciding a suspected fusion (vs. capture) and then to a second threshold, corresponding to a loss of capture.

This technique has the disadvantage of working in an "all-or-nothing" manner regarding the fusion: that is to say that anything that neither looks like a complete or partial capture or a loss of capture is considered in default as a fusion situation. In other words, it is a binary classification technique. This is not a fusion quantification technique that would evaluate more or less significant temporal lag on a scale between the stimulated and spontaneous depolarization waves (if the latter is present) respectively corresponding to the application of stimulation (evoked wave) and to the occurrence of spontaneous QRS complex.

In addition, this method produces a suitable result for suspecting a fusion situation when the AVD are short, but is not very discriminating for the long AVD range. In particular, the distinction between fusion and pseudo-fusion (if the depolarization is totally spontaneous in the presence of a stimulus that is applied too late) cannot be detected reliably.

EP 2756865 A1 describes another technique to not only determine the fusion situations, but also to quantify a fusion. This technique relies on the analysis of a unipolar EGM comparison with, for each cardiac cycle, the EGM recorded with two reference signals to produce two signed adaptive correlation indices (ASCI), between −1 and +1. These indices are then multiplied to reflect the more or less great resemblance of the cardiac cycle to recorded references, an intermediate position corresponding to a fusion, quantified by the product of the two indices calculated for the cardiac cycle.

However, this technique does not always highlight the fusion, the signal on the unipolar path not always sufficiently reflecting certain characteristic changes in morphology or in temporal synchronization produced by a fusion.

SUMMARY

The object of the present disclosure is to overcome these abovementioned drawbacks by proposing an improvement to the method of EP 2324885 A1 cited above, which allows not only to discriminate reliably effective fusion situations, but also to quantify the fusion degree in a method that accurately reflects the electrical activation resulting from the coincidence of two wave fronts, one from spontaneous depolarization, and the other induced by stimulation.

The disclosure is applicable to a wide variety of devices, both for conventional bradycardia pacing devices (wherein fusion is generally harmful and inappropriate in the case of a capture test) and CRT resynchronization devices (wherein notably a fusion between a left ventricular stimulation and a spontaneous contraction of the right ventricle, or vice versa can be optimized).

Furthermore, in the present disclosure a fusion by reference to ventricular stimulation and detection will be mainly described, but it must be pointed out that the present disclosure can also be applied to atrial stimulations and detections for determination of a fusion in the atrium (in this case it is the pacing rate that varies, not the AVD).

More specifically, the disclosure provides a device including:
Means of controlled stimulation of the heart;
Means for sensing ventricular and/or atrial depolarization signals, adapted to collect during a single cardiac cycle, concurrently on separate respective channels, at least two different signals of endocardial electrogram EGM, and to derive at least two respective distinct temporal components; and
Means of analysis of the current cardiac cycle, including:
means adapted to combine the at least two temporal components in at least one representative parametric 2D characteristic of said cardiac cycle, from the variations of one of the temporal components as a function of the other; and
means adapted to make a comparison of the 2D characteristic of the current cycle with at least one reference 2D characteristic previously obtained and stored by the device to derive a value representative of at least one descriptor of the similarity between the 2D characteristic of the current cycle and the reference 2D characteristic.

Typically, this device comprises means of quantifying a degree of fusion, comprising:
Means for performing a first comparison of the 2D characteristic of the current cycle with a first reference 2D characteristic previously obtained in complete capture situation and stored by the device, for deriving a first value of said at least one descriptor;
Means for performing a second comparison, from the 2D characteristic of the current cycle with a second reference 2D characteristic (Reference 2) obtained previously in ventricular spontaneous rhythm situation and stored by the device, to derive a second value of said at least one descriptor; and
Means for deriving a metric function to both said first value and said second value, said metric quantifying a fusion rate in a case of a fusion situation occurring between two respective extrema corresponding to said first and second values obtained respectively in a complete capture situation and in a spontaneous rhythm situation.

In some embodiments, said at least one descriptor includes two different descriptors defining a two-dimensional space of which two dimensions correspond to the two descriptors. Said first and second values are then represented by two respective points of the two-dimensional space, and said metric is calculated based on the respective distances between said two points of an origin mark of the two-dimensional space.

One of two different descriptors may include the correlation coefficient between the norms of the respective velocity vectors of the current 2D characteristic and of the first or second reference 2D characteristics, the other of the two descriptors being the average angle between the respective velocity vectors of the current 2D characteristic and of the first or second reference 2D characteristic.

Preferably, the fusion rate, expressed as a percentage of complete capture, is given for a current cycle in fusion closer to capture than to the spontaneous rhythm:

$$50+[50*(A2-A1)/(X2-X1)]$$

and for a current cycle in fusion closer to the spontaneous rhythm than to capture by:

$$50-[50*(B1-B2)/(Y1-Y2)].$$

A2−A1 is the difference of the distances A1 and A2, in said two-dimensional space, points respectively representing said first and second values for said current cycle in fusion closer to the capture than to the spontaneous rhythm.

B1−B2 is the difference of the distances B1 and B2, separating, in said two-dimensional space, points (P1, P2) respectively representing said first and second values for said current cycle in fusion closer to the spontaneous rhythm than to the capture.

X2−X1 is the difference of the distances X1 and X2 separating, in said two-dimensional space, points respectively representing said first and second values for cycles in complete capture.

Y1−Y2 is the difference of the distances Y1 and Y2, separating, in said two-dimensional space, points respectively representing said first and second values for cycles in spontaneous rhythm.

The means for establishing said first reference 2D characteristic may include:
  Means for application of stimulation with a short atrio-ventricular delay and a pacing rate greater than the spontaneous sinus rate, so as to obtain a series of cardiac cycles in a situation of complete capture; and
  Means of selection of a representative cardiac cycle from said cardiac cycles, and of determination from this representative cycle of said first corresponding reference 2D characteristic.

The means for establishing said second reference 2D characteristic may include:
  Means for application of stimulation with a long atrio-ventricular delay and a pacing rate greater than the spontaneous sinus rate, so as to obtain a series of cardiac cycles in situation of spontaneous ventricular rhythm; and
  Means of selection of a representative cardiac cycle from said cardiac cycles, and of determination from this representative cycle of said corresponding second reference 2D characteristic.

In some embodiments, means for validating said reference 2D characteristics are further provided, comprising:
  Means for performing a comparison of said first reference 2D characteristic with said second reference 2D characteristic, to derive at least one descriptor representative of the similarity between the first and second reference 2D characteristics; and
  Means for enabling or disabling said reference 2D characteristics depending on whether said at least one descriptor satisfies or does not satisfy at least one predetermined validation criterion.

In some embodiments, the device includes:
  Means for application of stimulation with a long atrio-ventricular delay and a pacing rate lower than the spontaneous sinus rate, so as to obtain a series of cardiac cycles with spontaneous depolarization, for both atrial and ventricular, situations;
  Means of selection of a cardiac cycle representative from said cardiac cycles, and of determination from this representative cycle of a third corresponding reference 2D characteristic; and
  Means of determination, from said second and third reference 2D characteristics, of an offset value between stimulated atrial event and spontaneous atrial event.

BRIEF DESCRIPTION OF THE DRAWINGS

Further features, characteristics and advantages of the present disclosure will become apparent to a person of ordinary skill in the art from the following detailed description of exemplary embodiments of the present disclosure, made with reference to the drawings annexed, in which like reference characters refer to like elements and in which.

DETAILED DESCRIPTION

An embodiment of the device of the present disclosure will now be described.

With regard to software aspects, the disclosure may be implemented by an appropriate programming of control software of a known stimulator, for example of a pacemaker, a resynchronizer and/or a defibrillator, including means for acquisition of a signal provided by endocardial leads and/or one or more implanted sensors.

The disclosure may be implemented in implantable devices such as those of the families Reply, Paradym, Intensia, Paradym RF and Platinium, produced and marketed by Sorin CRM, Clamart, France.

These devices include programmable microprocessor circuitry to receive, format and process electrical signals collected by implantable electrodes, and deliver stimulation pulses to these electrodes. It may be possible to download, by telemetry software that is stored in memory and executed to implement functions, the functions of the disclosure that are described below. The adaptation of these devices to the implementation of the functions of the disclosure are within the skill in the art and will not be described in detail.

A method of the disclosure is implemented primarily by software means, with appropriate algorithms automatically and repeatedly executed by a microcontroller or a digital signal processor.

For the sake of clarity, the various processing applied are broken down and schematically by a number of distinct functional blocks, but this representation, however, has only an illustrative purpose, these circuits comprising common elements and corresponding in practice to a plurality of functions generally performed by the same software.

Figure 1:
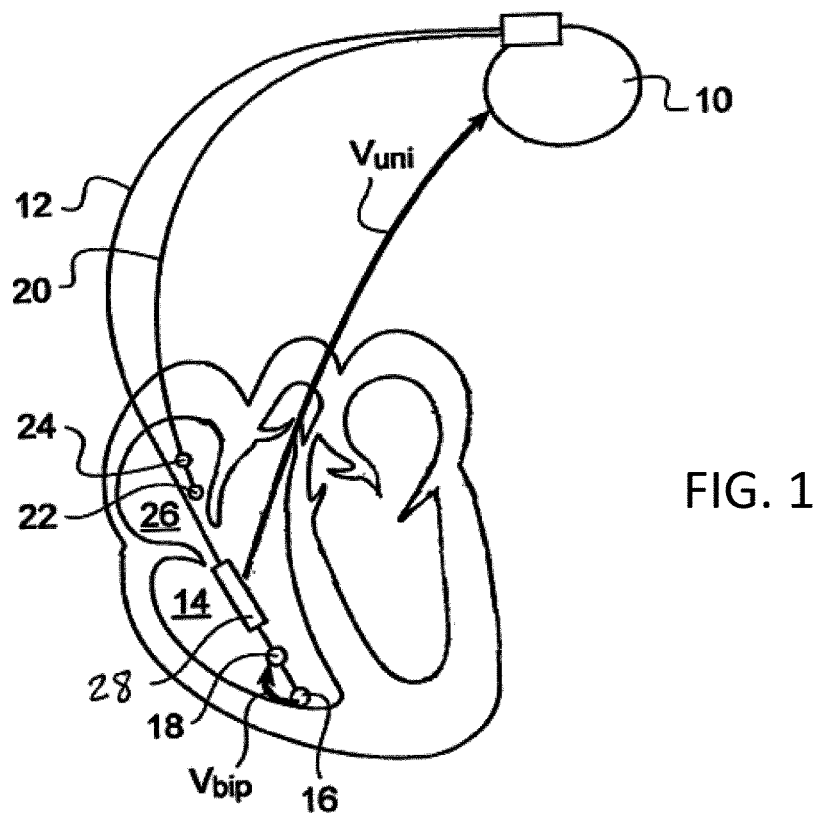
FIG. 1 is a general view showing a "dual chamber" bradycardia pacing device, with a generator and a lead implanted in a right chamber of the heart.

FIG. 1 illustrates a configuration of "dual chamber" bradycardia pacing in which a pulse generator 10 is associated with a first lead 12 implanted in the right ventricle 14. The head of the lead comprises two electrodes, namely a distal electrode (tip) 16 and a proximal electrode (ring) 18. A second lead 20 is provided with atrial distal 22 and proximal 24 electrodes for detection located at the right atrium 26 for the detection of signals in this cavity and possible application of an atrial stimulation (alternatively, these atrial electrodes 22, 24 may be floating electrodes arranged on the lead 12 at the atrium level).

In some embodiments, the right ventricular lead 12 may also be provided with a ventricular winding (coil) 28 forming a defibrillation electrode and also to collect an endocardial signal (this winding may be used instead of the proximal ring electrode 18).

As will be described in detail below, a technique of the disclosure implements a combination of two separate endocardial electrogram signals collected simultaneously, such as the signals from the same ventricular cavity, for example the right ventricle.

Figure 2:
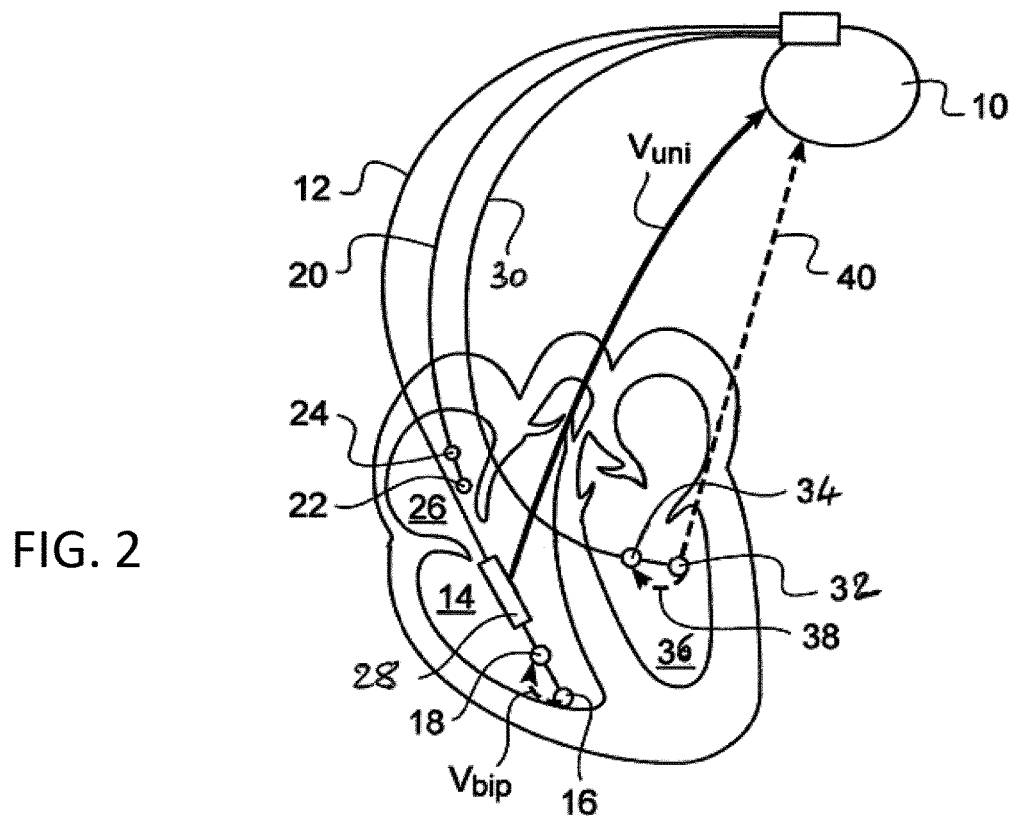
FIG. 2 is a general view showing a CRT stimulation device with a generator and right and left cardiac leads implanted in the heart.

FIG. 2 illustrates another embodiment of a pacing configuration in which the disclosure may be applied, namely a biventricular pacing, in order to restore the synchronization between the two ventricles.

The pulse generator 10, in addition to elements 12-18 described above, is provided with a third lead 30, for example a lead disposed in the coronary network, with one or more electrodes 32, 34 disposed adjacent the left ventricle 36 (in the case of a "multi-electrode" left lead, the left lead may also include one or more intermediate electrodes located in a middle position between the electrodes 32 and 34). It is thus possible to provide simultaneous stimulation, or with a slight controlled temporal delay (interventricular delay VVD), of both right and left ventricles to restore synchronization between the two cavities and improve overall patient hemodynamics. In the case of a multi-electrode left lead, a multisite pacing to treat a disorder of intraventricular synchronism can also be applied.

With regard to stimulation of the left ventricle, a bipolar configuration (between the two electrodes 32 and 34 of the lead 30) or a unipolar configuration (between one of the electrodes 32 or 34 and the box can) of the generator 10 may be used. A quadripolar lead may also be used for those purposes. The corresponding two "stimulation vectors" are referenced 38 and 40 in FIG. 2. These same vectors can also be used for collecting a signal of left ventricular depolarization. In the case of a multipolar lead there may be a large number of bipolar and unipolar possible vectors defined from each of the electrodes (one can also simultaneously use multiple left vectors, in the embodiment mentioned above a left multisite pacing).

Figure 3:
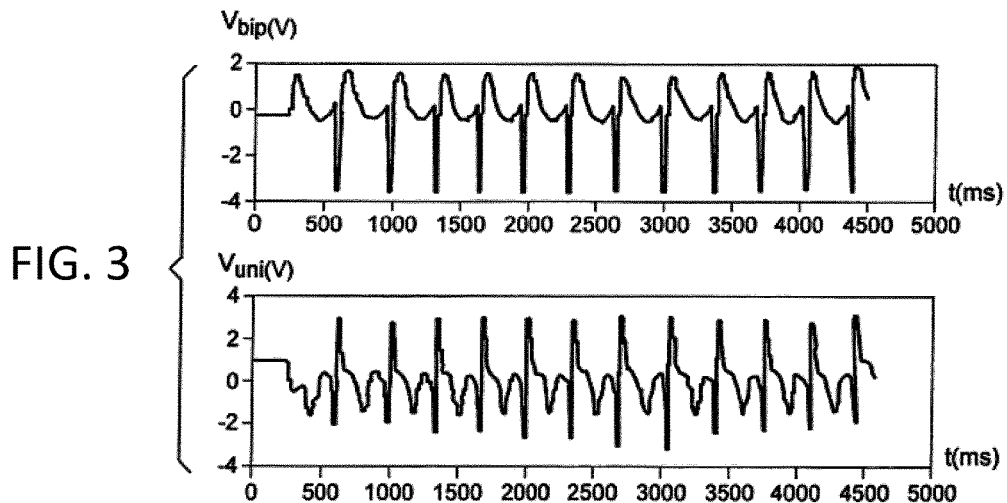
FIG. 3 is an example of EGM signals obtained on bipolar ventricular and unipolar ventricular channels, respectively, of one of the leads of FIG. 1.

FIG. 3 illustrates an example of EGMs plots Vbip and Vuni respectively observed on the ventricular bipolar channel and the ventricular unipolar channel of the configuration of FIG. 1 or FIG. 2.

In some embodiments, the EGMs collected for this purpose in the right ventricle may include:

A right ventricular component Vbip derived from a bipolar near-field EGM signal collected between the distal electrode 16 and the proximal electrode 18 of the right ventricular lead 12, and Another right ventricular component Vuni derived from a unipolar EGM far-field signal collected between the defibrillation coil 36 of the right ventricular lead 12 and the metal housing 10 of the generator.

Other configurations can be used, from far-field signals (e.g between one of the electrodes 16 or 18 and the housing 10, or between the electrodes 18 and 32) and t near-field signals (for example between two electrodes 32 and 34 of the ventricular lead).

Figure 4:
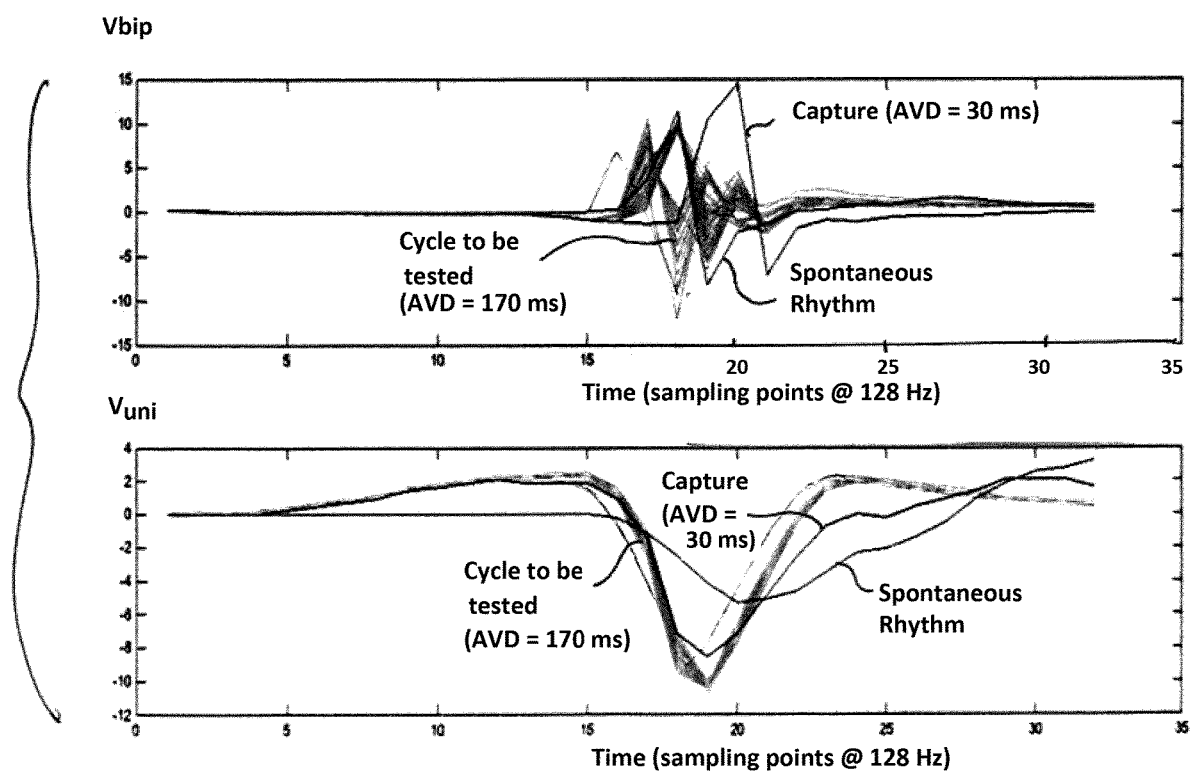
FIG. 4 shows examples of signals collected from a bipolar channel and from a unipolar channel for different situations corresponding to complete ventricular capture, to a total loss of capture allowing the spontaneous ventricular rhythm to appear, and a number of intermediate cycles to be tested, with a possible presence of a more or less marked fusion, for intermediate AVD between the two situations of capture and of loss of capture.

FIG. 4 shows examples of signals collected on a bipolar channel (Vbip) and on a unipolar channel (Vuni) for different situations corresponding to a complete capture, to a total loss of capture allowing the spontaneous ventricular rhythm to appear, and for a number of intermediate cycles to be tested, with the presence of a possible more or less marked fusion, for intermediate AVD between the two situations of capture and of loss of capture.

As shown, the information is not the same on the bipolar and unipolar channels and, for example, the fusion cycles (in this example, with an AVD of 170 ms) are much morphologically closer to the spontaneous rhythm than to capture on the bipolar EGM, and much closer to capture on the unipolar EGM.

Considering only the unipolar EGM, the difference is much less marked between fusion cycles and reference cycles with complete capture which would lead, if one wanted to quantify the fusion, as a percentage of fusion (expressed as a percentage of capture) much more important than reality.

For these and other reasons, the present disclosure seeks to optimize the detection and quantification of the ventricular capture by adding a second reference corresponding to a spontaneous ventricular rate in order to identify the degree of fusion in two ways—firstly with respect to a complete capture and secondly in relation to a spontaneous rhythm—and also the gradual transition between fusion and spontaneous rhythm for the longest AVD.

The combination of both bipolar and unipolar components into a unique characteristic enables the device to have a reference containing all information available from the EGM more globally, which quantifies accurately and robustly a possible fusion present with the current cardiac cycle.

Both bipolar and unipolar signals are combined into a single feature type "heart loop" or "vectogram" (VGM), which is the representation in a two-dimensional space of one of the two EGM signals (in ordinate) relative to the other (in abscissa). Each cardiac cycle is then represented by a vectogram in the plan {Vbip, Vuni} thus defined, a vectogram the geometry of which (shape of the curve) thus ignores the temporal dimension—which only intervenes as a parameter describing the method the curve is traversed.

This "vectogram" (VGM), which is obtained from electrogram signals (EGM) from intracardiac leads, should not be confused with the "vectocardiogram" (VCG), which is obtained from electrocardiogram (ECG) signals from external electrodes placed on the patient's chest.

The construction of a VGM and its analysis to quantify cardiac data are described for example in Milpied et al., "Implantable Cardioverter Arrhythmia Discrimination in Defibrillators using Support Vector Machines Applied to a New Representation of Electrograms," IEEE Transactions on Biomedical Engineering, June 2011, 58 (6): 1797-1803.

The analysis of a VGM has also already been proposed, as stated in the introduction, from EP 2324885 A1 (Sorin CRM) to decide there is a fusion suspicion in order to invalidate a capture test.

Note also that the "bi-dimensional" or "two-dimensional" analysis (2D) mentioned herein should not be construed so as itself limited. The disclosure can indeed apply equally to an analysis in a multidimensional space of higher order (3D or more), by extrapolating the teachings of the present description to a situation wherein EGM signals from the same cavity are collected simultaneously on three channels or more.

Figure 5:
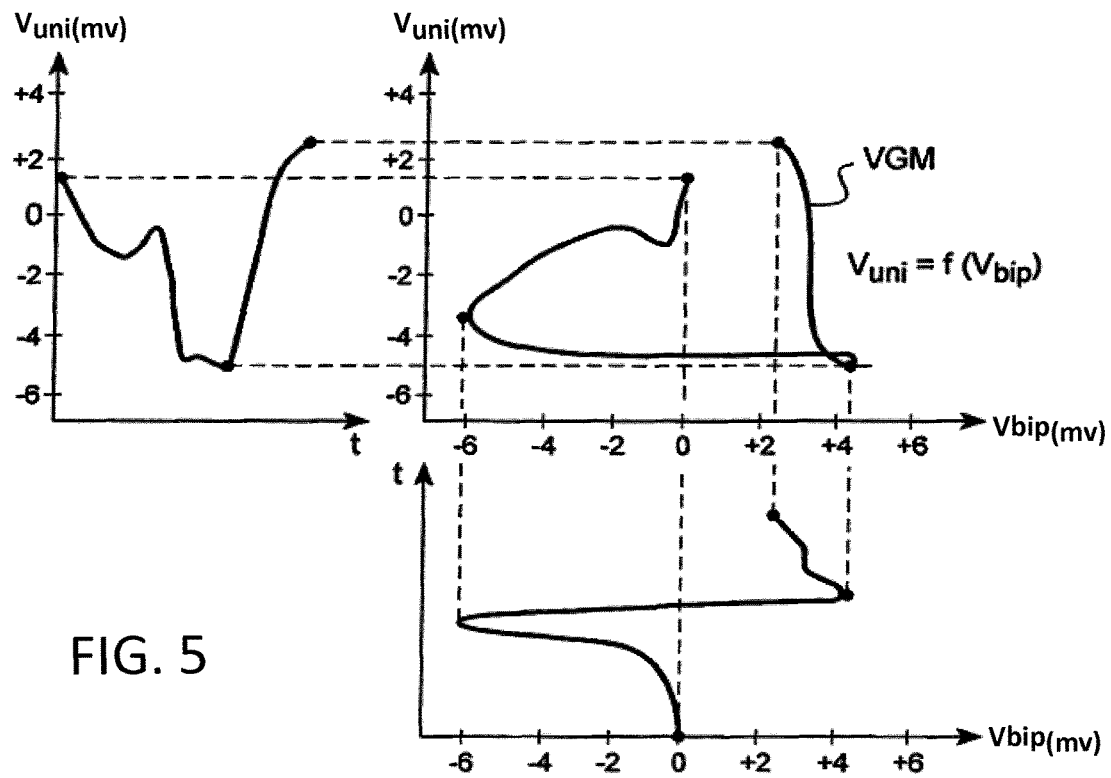
FIG. 5 shows a method to combine bipolar and unipolar signals collected in a single ventricular cavity to build a two-dimensional vectogram characteristic.

As shown in FIG. 5, the collected EGM signals Vuni(t) and Vbip(t) are sampled, and the successive samples of the two components are stored and then combined to produce a parametric curve (the characteristic VGM), VGM=(Vbip(t), Vuni(t)) or {x=Vbip(t), y=Vuni(t)}.

This curve is a curve parameterized by time, plotted from the variations of one of the temporal components (Vuni) as a function of the other (Vbip). It is a vectogram (VGM) representative of the cardiac cycle to be analyzed, and is also denoted "parametric 2D characteristic." It is graphically in the form of a loop in which time only appears in the method through the loop on the cycle.

Figure 6:
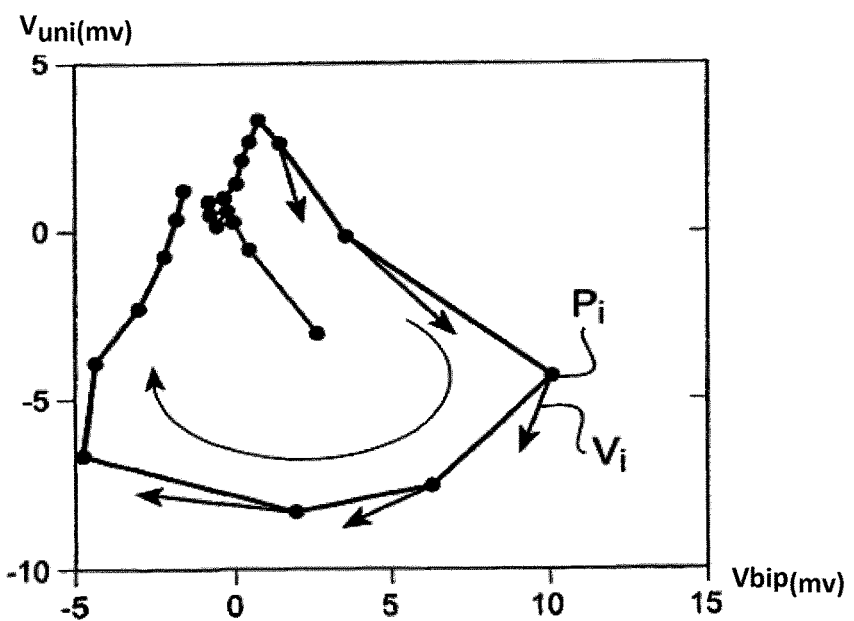
FIG. 6 is an example of vectogram obtained for a sampled cardiac cycle at 128 Hz, with a representation of the velocity vectors in various successive points.

In practice, as shown in FIG. 6, sampling produces an open polygon VGM wherein each vertex corresponds to a sampling point of the measurement of the signal Vuni and Vbip of the EGM. In the example of FIG. 6, sampling is carried out at a frequency of 128 Hz, which gives about 11 measurement points for a time interval of 80 ms, these values being stored to be analyzed (therefore, it is possible to maintain a greater number of points in memory, for example 60 points, the comparison between two vectograms being made, however on a smaller number of points, typically 11 or 21 points).

The shape of the velocity vector Vi in various successive points Pi of the VGM for a sampling frequency of 128 Hz is also shown in FIG. 6. At a given point, the speed is vector data (the speed being defined by its orientation and norm), and the velocity vector can be calculated at each point of the VGM from a discrete filter that approximates the first derivatives Vbip(t)/dt and Vuni(t)/dt which for a sampled characteristic, can be calculated from the previous point and the next point on the curve.

The collected VGM characteristic is stored as a series of descriptive parameters based on the velocity vectors in each point of the curve and including the norm of the velocity vector and the direction of the velocity vector, i.e. the angle it makes with respect to the axis of the abscissa of the VGM.

Various embodiments of the disclosure will now be described.

The disclosure proposes to operate a morphological comparison between, first, the current VGM (stored in the form of values of norms and angles of velocity vectors at different sampling points) and, second, two reference VGMs (stored as counterpart descriptors), one obtained in situation of complete capture of the ventricle and the other obtained in situation of exclusively spontaneous rhythm in the ventricle, that is to say with a fusion rate of 0% in terms of capture percentage.

The comparison between the VGM of the current cycle and of these two reference VGMs allows, in case of detection of a fusion (that is to say, a situation that is neither that of a full capture nor that of a ventricular spontaneous rhythm), evaluate a fusion rate, thereby allowing the device to quantify by a metric the long temporal shift between the evoked depolarization wave consecutive to stimulation, and the wave of spontaneous depolarization related to natural rhythm.

The comparison between the VGM of the current cycle and any of the reference VGMs is to quantify the similarities from:
The correlation coefficient C between the norms of the respective velocity vectors of the current VGM and of the reference VGM, and
The average value $\theta$ of the angle between the respective velocity vectors of the current VGM and the reference VGM.

The curves may be considered similar if C (which reflects the correlation between the velocity vectors of the norms is sufficiently large, that is to say close to unity, and $\theta$ (which reflects the orientation angular differences) is small enough, that is to say close to zero. The more the value of C is far from 1 and the more that of $\theta$ is from 0, the more the two VGMs are dissimilar.

The use of C and $\theta$ parameters for operating the comparison between two VGMs is not limiting, and other parameters may be used. Similarly, the combined use of C and $\theta$ is particularly advantageous, but it would also be possible to assess the similarity of VGMs from only one of the two C or $\theta$ parameters, or from a larger number of parameters, three parameters and more. The descriptors C and $\theta$ are preferred, however, due to their low sensitivity to artifacts and to the relative ease to calculate them.

Figure 7:
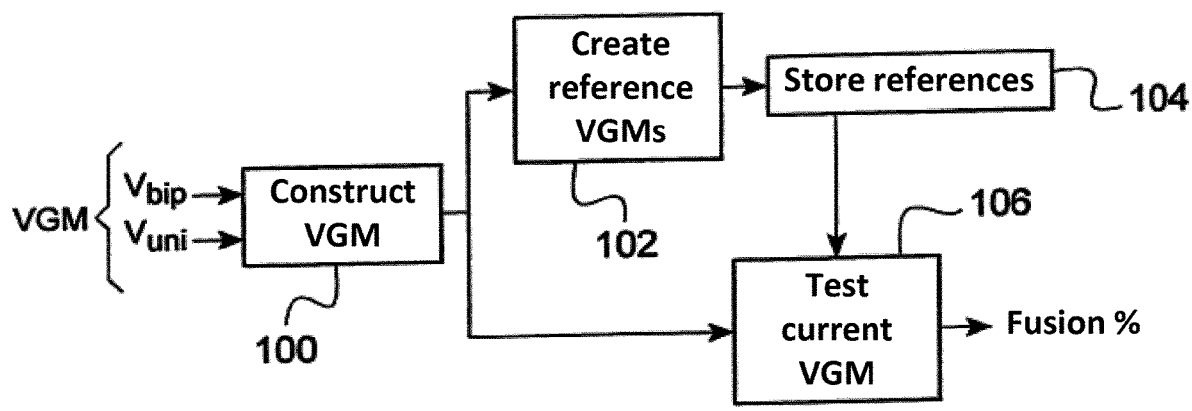
FIG. 7 is a block diagram illustrating an implementation of the disclosure.

FIG. 7 illustrates in very general terms a method in which the device of the disclosure is implemented.

From the collected bipolar and unipolar EGMs, a VGM is built (block 100). Previously, two reference VGMs are constituted in stable conditions (slow sinus rhythm, preferably overnight) (block 102, detailed FIG. 11) and stored in memory (block 104). The current VGMs are subsequently compared (block 106) to the two stored reference VGMs, for outputting a metric quantifying a fusion rate between 0 and 100%.

In the following, the "fusion rate" is expressed in terms of rate of spontaneous rhythm—that is to say, a fusion rate of 0% corresponds to a complete capture and a fusion rate of 100% corresponds to a situation of entirely spontaneous rhythm—but we could also express this fusion rate relatively to a capture situation, the fusion rate ranging then from 100% to 0% in the opposite direction.

Figure 8:
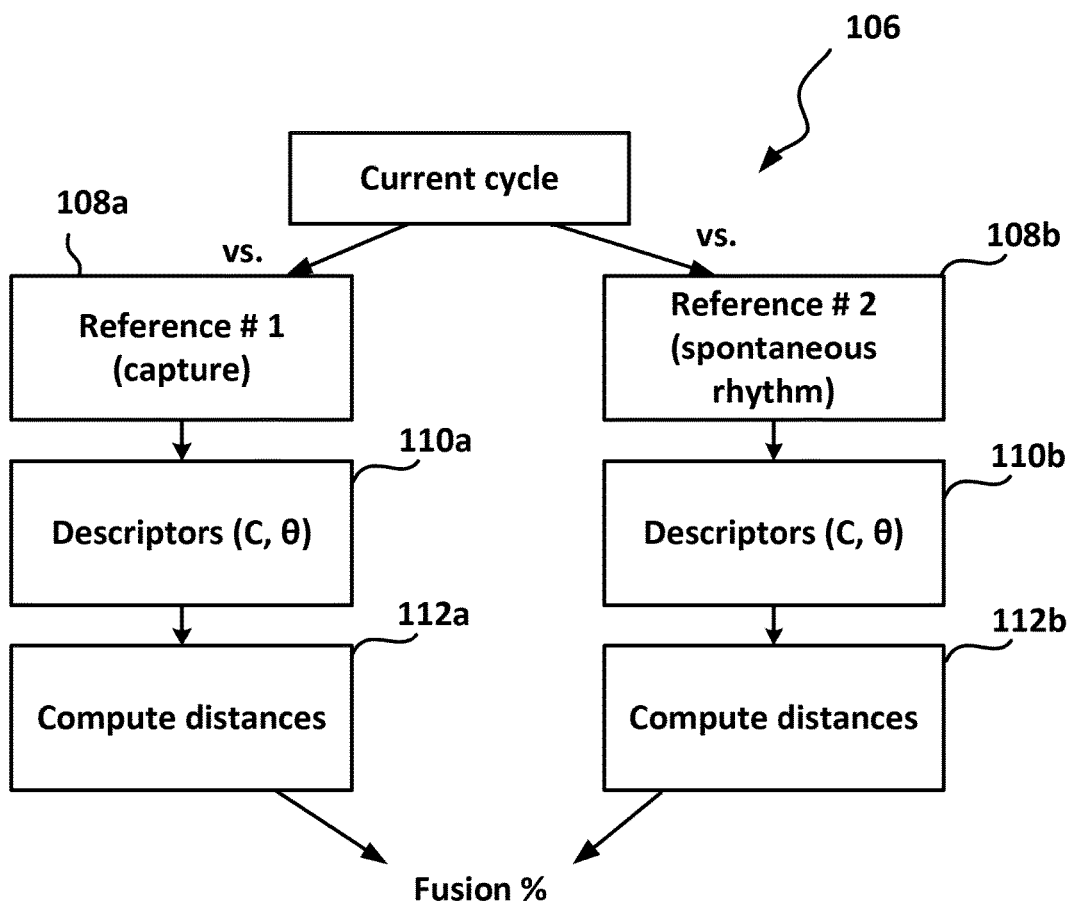
FIG. 8 is a simplified flow chart showing a sequence of steps performed for an analysis of a current cycle.

FIG. 8 shows the test of block 106, in the form of a simplified flowchart showing a sequence of steps performed for the analysis of a current cycle.

The VGM of the current cycle is compared to both the reference VGM corresponding to a complete capture situation, hereinafter "Reference #1" (108a block) and to the VGM corresponding to a situation of ventricular spontaneous rhythm, hereinafter "Reference #2" (108b block).

Figure 9:
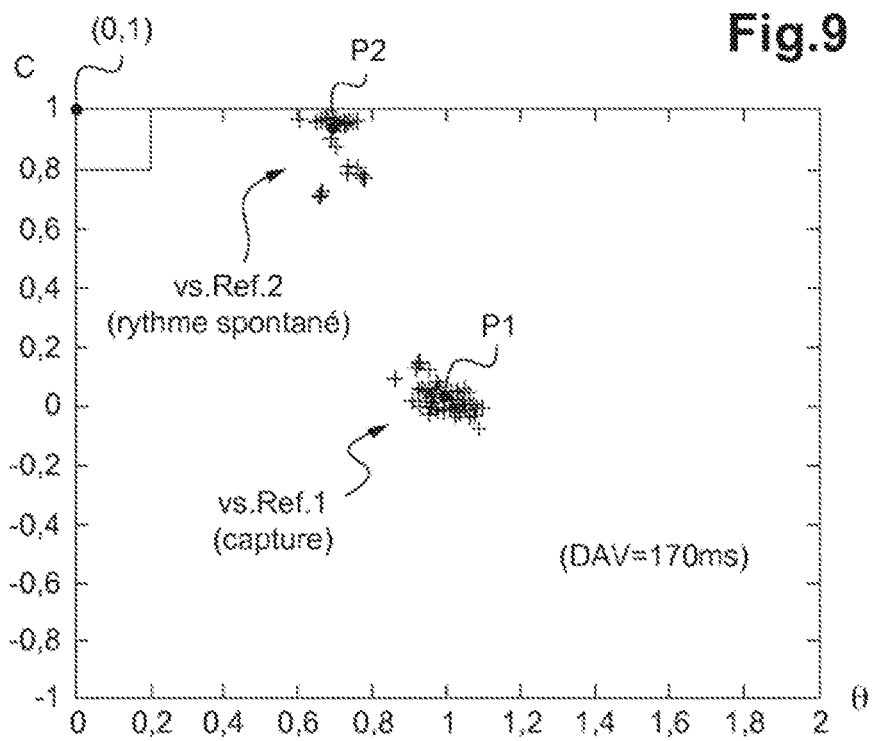
FIG. 9 is a representation, in two-dimensional space, of clouds of points corresponding to various pairs of values of recorded descriptors, on a number of current cycles, during comparison with the two references respectively corresponding to a ventricular capture and to a spontaneous ventricular rhythm.

Both comparisons produce two respective pairs of descriptors C and $\theta$ (blocks 110a and 110b), which can be represented in a two-dimensional space shown in FIG. 9. The next step (blocks 112a and 112b) is to calculate the distances of the various points [C, $\theta$] of the two-dimensional space corresponding to the descriptors obtained relative to the origin [0,1] of the same space, to determine, from these distances and in the method described below a metric quantifying a fusion rate of the current cycle.

FIG. 9 illustrates, in the two-dimensional space of which the two dimensions correspond to the two descriptors C and θ, an example of distribution of the points obtained for a few tens of current cycles with a same AVD adjusted in this case to 170 ms. This example shows two point clouds, one obtained by comparing current cycles with the Reference #1 (full capture), the other by comparison with the reference #2 (spontaneous ventricular rhythm). Points P1 and P2 indicate the respective barycentres of the two point clouds. The point [0.1] is an ideal theoretical situation wherein the current cycle is identical to one or the other of reference cycles, with a correlation coefficient C equal to unity and an average angle θ zero between the respective velocity vectors of the two VGMs.

The comparison of the VGMs of the current cycles with each of Reference #1 and Reference #2 is evaluated:
- Either by comparison with predetermined thresholds on C and/or θ: for example it is considered that the curves are similar if C>Threshold 1 and θ<Threshold 2;
- Or by a relation between C and θ: for example it is considered that the curves are similar if C>θ;
- Or, preferably, using the distance calculated in the plan [C θ] of the descriptors between the current point and the point [0.1]: the smaller the distance, the more the VGMs are similar.

In the example shown, the distance between each of the points P1 and P2 and the point of origin [0,1], we find that the results of the two respective comparisons show that the cloud of points of comparison with Reference #2 (spontaneous rhythm) is closer to the original than the cloud of points of comparison with the reference #1 (full capture), which means that current cycles are, in fusion, closer to a spontaneous ventricular rhythm than to a complete capture—so with a fusion rate, expressed as a percentage of capture, less than 50%—but they are not sufficiently close to the point [0,1] to conclude to a purely spontaneous rhythm.

Figure 10:
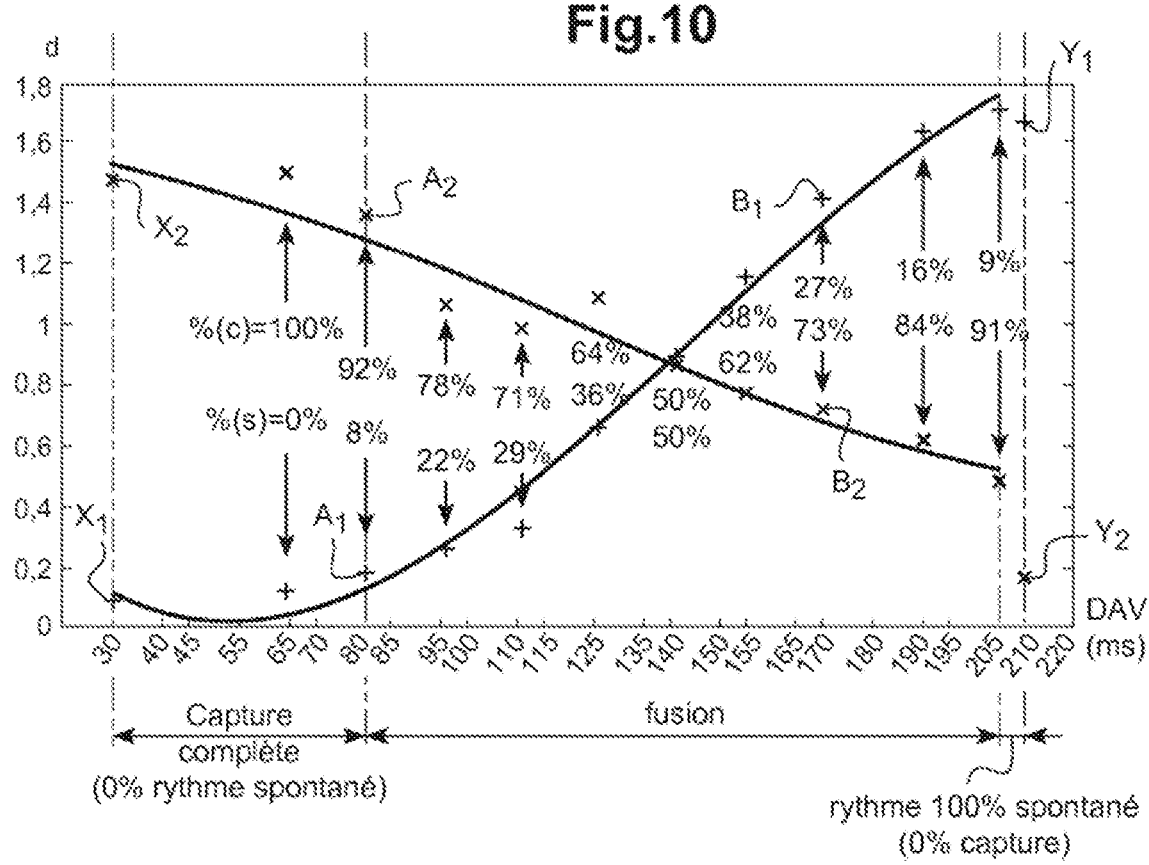
FIG. 10 is an illustration showing variations in a distance between points of the space of FIG. 9 and an origin of the same space, for increasing values of the AVD.

FIG. 10 is a representation in which the AVD varied between all possible adjustment values, from a minimum value AVD=30 ms producing in all circumstances a full capture of the ventricle, to a maximum value of AVD long enough to let the spontaneous rhythm occur. In ordinate, the distance between the origin [0,1] of the two-dimensional space of FIG. 9 is plotted and the point [C θ] resulting from the comparison with the reference #1 (points represented by "+") or with the Reference #2 (points represented by "x").

For a minimal AVD, AVD=30 ms in complete ventricular capture, X1 and X2 marks are respectively obtained, and for a maximum AVD (here 210 ms), the respective marks Y1 and Y2 are obtained.

In the figures fusion percentages have also been expressed in terms of capture percentages ("% (C)") and in terms of spontaneous rhythm percentages ("% (S)").

If the current cycle in fusion is closer to a capture than to a spontaneous rhythm (left part of FIG. 10, A1 and A2 marks), then the capture percentage is greater than 50% and the spontaneous rhythm percentage is less than 50%. Conversely, if the current cycle in fusion is closer to a spontaneous rhythm than to a capture (right part of FIG. 10, B1 and B2 marks corresponding to the points P1 and P2 of FIG. 9), then the capture percentage is less than 50% and the spontaneous rhythm percentage is greater than 50%.

The difference between the X1 and X2 marks obtained in complete capture quantifies the degree of fusion, a difference which, in this example, is of the order of X2−X1=1.4.

Similarly, the difference between Y1 and Y2 in complete spontaneous rhythm is of the order of Y1−Y2=1.6.

In the case of a current cycle in fusion closer to the capture than to the spontaneous rhythm (marks A1 and A2, where A2>A1), one should always have A2−A1<1.4, and should roll away from the capture (A1>X1) and should get closer to the spontaneous rhythm (A2<X2).

If A2>A1 and A2−A1<X2−X1 and if A1>X1 and A2<X2 (with a tolerance, such as a tolerance of ±0.1), then the percentage of capture will be:

$$50+[50*(A2-A1)/(X2-X1)].$$

Otherwise, no degree of fusion will be calculated for the cycle in question, which possibly corresponds to an extra-systole and does not follow the expected increase.

A percentage of capture above a given threshold, for example greater than 95%, corresponds to a situation of complete capture and not of fusion. The percentage of spontaneous rhythm can then be calculated as:

$$100-\text{the percentage of capture.}$$

If the current fusion cycle is closer to the spontaneous rhythm than to capture (marks B1 and B2, where B1>B2), the calculation of the percentage of spontaneous rhythm can be based on the distance between marks Y1 and Y2 in spontaneous rhythm.

For a current cycle in fusion a value B1−B2<1.6 may be obtained, may get closer to capture (B1<Y1) and may roll away from the spontaneous rhythm (B2>Y2).

If B1>B2 and B1−B2<Y1−Y2 and if B1<Y1 and B2>Y2 (with a tolerance, such as a tolerance of ±0.1), then the percentage of spontaneous rhythm will be:

$$50-[50*(B1-B2)/(Y1-Y2)].$$

Otherwise, no degree of fusion will be calculated for the cycle in question.

A higher percentage of spontaneous rhythm at a given threshold, for example greater than 95%, corresponds to a situation of spontaneous rhythm and not fusion.

The percentage of capture may be calculated as:

$$100-\text{the percentage of spontaneous rhythm.}$$

The final fusion rate can be expressed in terms of capture rate, in terms of spontaneous rhythm rate, or by a combination of these two rates.

Figure 11:
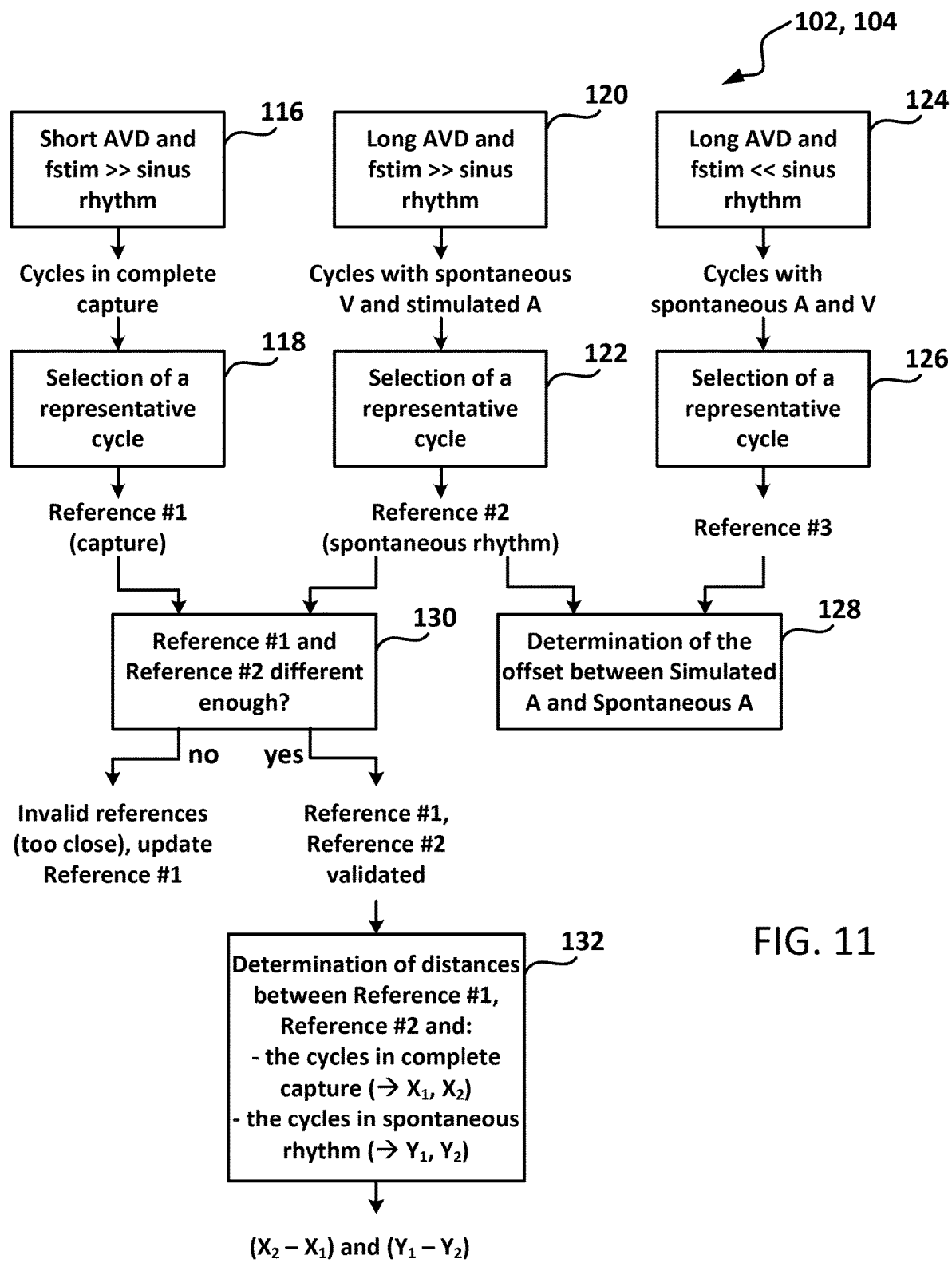
FIG. 11 is a flowchart showing a sequence of steps performed during a preliminary development of the two references used for the determination of a degree of fusion of a current cycle.
Figure 12:
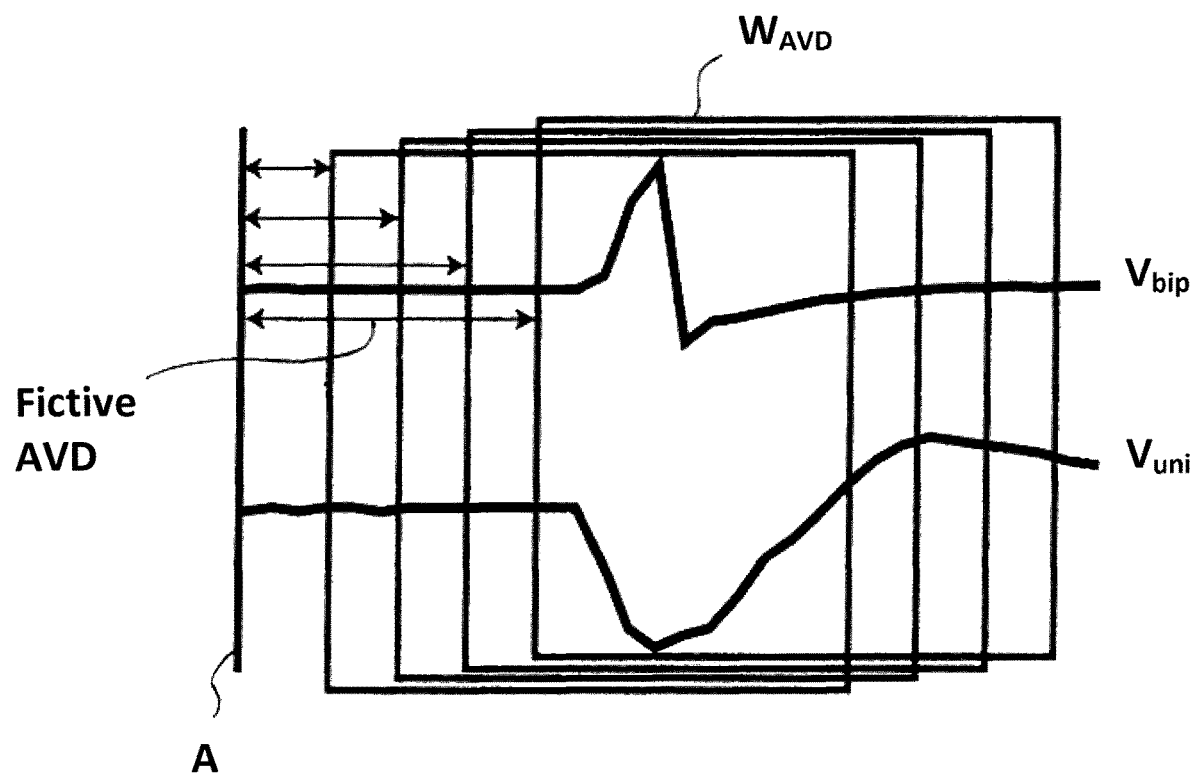
FIGS. 12 and 13 illustrate two different windowing techniques for comparing a cycle to be tested with a reference in spontaneous ventricular rhythm.
Figure 13:
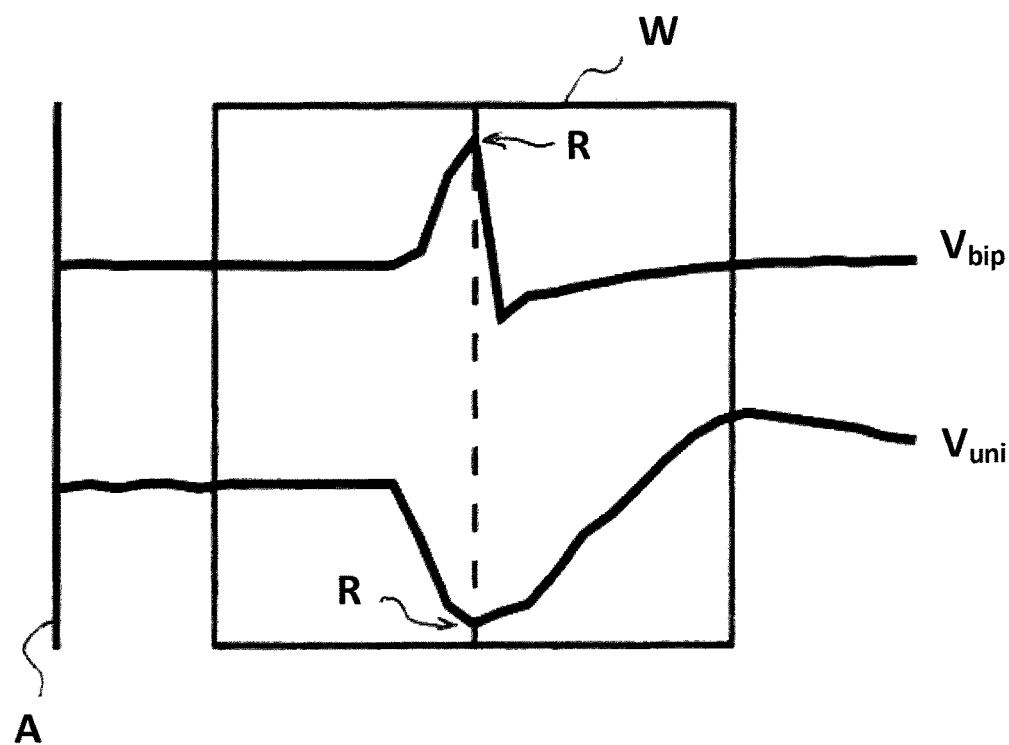

Referring to FIGS. 11 to 13, a method to obtain two references used for determining the fusion rate will now be described.

These references are created and updated on a periodic basis and in stable conditions (e.g., at night), for example, once a day or once a week.

To establish the reference in complete capture (Reference #1), the AVD is set to the shortest possible value, i.e. AVD=30 ms, preferably with atrial pacing at a significantly higher stimulation frequency than sinus rhythm (block 116) to be as far as possible from the onset conditions for a possible fusion.

A plurality of cycles in complete capture are stored in these conditions, and compared in order to establish or select a single representative cycle (block 118). One method is to record multiple VGMs and to compare them two by two, and then verify that a minimum number of VGMs, for example two VGMs, are alike. Another method is to look at, as the cycles are recording, two VGMs which are alike, with a maximum number of VGMs to be tested, for example five VGMs. If there is sufficient similarity between cycles, then the Reference #1 is created and stored, either by selecting one of the cycles, either by averaging cycles which are similar.

For reference in spontaneous rhythm (Reference #2), a very long AVD is programmed, for example AVD=300 ms, to let the spontaneous rhythm be expressed before stimulation (block 120).

A plurality of cycles are thus produced in the same method as for complete capture cycles, and Reference #2 is similarly created by determining a single representative cycle (block 122) after comparing the different produced cycles.

However, for the establishment of this Reference #2 a wider measurement window is necessary because part of the EGM used for the subsequent comparison of the cycles to be tested will depend on the AVD of said cycles to be tested. In addition, the moment of occurrence of the depolarization is not the same in the case of a stimulated atrial event (event A) than in that of a spontaneous atrial depolarization (P event).

A first possibility is to establish two separate references in spontaneous ventricular rhythm, one with a stimulation of the atrium and the other with spontaneous depolarization of the atrium (sinus rhythm).

An alternative, preferred solution, is to establish a unique reference, for example with stimulated depolarization of the atrium, and to predict a temporal compensation value or offset, determined as the difference of the recognized conduction time in the ventricle for spontaneous atrial depolarization (P) and for a stimulated trial depolarization (A): offset=AR−PR.

This offset is established by a temporary programming of a long AVD with a much lower pacing rate than sinus rhythm (block 124), then selection, as above, of a representative cycle (block 126) to obtain a provisional reference (Reference #3) for determining the offset above (block 128).

In a simplified variant, this offset can be established for the calculation of the Reference #2 by measuring AR intervals and PR intervals, without reference #3, but only under the conditions of long AVD and low stimulation frequency (block 124), on a few cycles (8 cycles, for example) and by taking the difference between the average value of AR intervals and the average value of the PR intervals.

Once the two references Reference #1 and Reference #2 are established, a final step is to compare these two references by applying a fictitious AVD 30 of ms and an offset if necessary (so that the condition of the atrium and the AVD are the same). Both references are then compared (block 130).

If the Reference #1 is in complete capture, then the depolarization of Reference #2 should arrive later than that of the Reference #1 (no overlap in time), the comparison of curves giving a significant difference between the references. References are then validated and analyzed (block 132) to determine the marks X1, X2 and Y1, Y2 and the differences X2−X1 and Y1−Y2 (block 132).

If, however, the distance in the two-dimensional space of descriptors C and θ between the current point and the point [0,1] is less than a given threshold, for example less than unity, then it is considered that the references are too close, the Reference #1 being probably already in fusion and not full capture. It may not be possible to determine the correct degree of fusion and Reference #1 is invalidated as a reference for complete capture.

In the latter case, it may be possible to repeat the calculation of the Reference #1 in producing a plurality of additional cycles in the VVI mode at a frequency higher than the patient's base frequency, e.g. at 100 bpm to retrieve a reference in complete capture. If so, it may be sufficient to compare all the resulting cycles to the Reference #2 and select the cycle that differs the most while being very close to the evoked response with AVD=30 ms, the selection being made as above by applying thresholds to the values of θ and C. Another possibility is to use an older Reference #1 (if it exists) and to revalidate Reference #1 with the new Reference #2.

FIGS. 12 and 13 illustrate two different windowing techniques for comparing the test cycle with the reference in spontaneous rhythm.

An AVD is applied to the current cycle to compare a current stimulated cycle with the reference in spontaneous rhythm, while the reference cycles were achieved without AVD.

As shown in FIG. 12, for comparing test cycles stimulated with variable AVD to Reference #2 in spontaneous rhythm, the device applies a "fictitious AVD" (fictitious because it is in spontaneous rhythm) added to the offset in a case of non-stimulation of the atrium, thereby producing a shift in the analysis window WAVD of bipolar and unipolar EGMs. The device may have a single Reference #2 regardless of the value of the programmable AVD (e.g., from 30 to 250 ms). For example, to test a cycle with atrial stimulation and AVD of 125 ms, Reference #2 may be used with a fictitious AVD of 125 ms. The sequencing of the EGMs in relation to atrial A marker may be as important as the morphology of the signals when it comes to comparing two VGMs obtained from respective bipolar and unipolar EGM signals.

FIG. 13 illustrates an embodiment of using, instead of the moving window of FIG. 12, a single window W centered on the characteristic peak (extreme R) of the EGM signal Vbip or Vuni, regardless of the type of atrial, spontaneous or stimulated, depolarization. However, this solution may not be optimal because it ignores the conduction delay.

What is claimed is:

1. An active implantable medical device comprising:
    memory having instructions stored thereon that, when executed by one or more processors, cause the processors to perform operations comprising:
        capturing, by one or more electrodes, at least two endocardial electrogram (EGM) signals during a first cardiac cycle;
        deriving, from the at least two EGM signals, at least two distinct temporal components;
        combining the at least two temporal components to generate a first parametric curve representative of the first cardiac cycle; and
        comparing the first parametric curve with a first reference curve corresponding to a complete capture situation to generate a first value for at least one descriptive parameter;
        comparing the first parametric curve with a second reference curve corresponding to a ventricular spontaneous rhythm situation to generate a second value for the at least one descriptive parameter; and
        in response to an occurrence of a fusion situation, generating a metric that quantifies a fusion rate for the fusion situation based on the first value and the second value.

2. The device of claim 1, wherein the first reference curve and the second reference curve are two-dimensional (2D) characteristics representing reference cardiac cycles.

3. The device of claim 1, wherein the at least one descriptive parameter includes two different descriptive parameters defining a two-dimensional (2D) space, the first value and the second value represented by two respective points in the 2D space, and wherein the metric is calculated based on a distance between each of the two respective points and an origin of the 2D space.

4. The device of claim 2, wherein at least one of the two different descriptive parameters is a correlation coefficient between norms of respective velocity vectors of the first parametric curve, the first parametric curve, and the second parametric curve.

5. The device of claim 2, wherein at least one of the two different descriptive parameters is an average angle between the respective velocity vectors of the first parametric curve, the first parametric curve, and the second parametric curve.

6. The device of claim 1, wherein the fusion rate is expressed in terms of a percentage of complete capture, the percentage of capture calculated as $$50 + \left(50 \times \frac{(A_2 - A_1)}{(X_2 - X_1)}\right)$$

for situations in which the first cardiac cycle is closer to a complete capture than to a spontaneous rhythm and as $$50 - \left(50 \times \frac{(B_1 - B_2)}{(Y_1 - Y_2)}\right)$$

for situations in which the first cardiac cycle is closer to the spontaneous rhythm than to the complete capture, wherein:
   $A_1$ and $A_2$ are points on the first parametric curve in situations where the first cardiac cycle is closer to a complete capture than to a spontaneous rhythm,
   $B_1$ and $B_2$ are points on the first parametric curve in situations where the first cardiac cycle is closer to the spontaneous rhythm than to the complete capture,
   $X_1$ and $X_2$ are points on the first or second reference curves in the complete capture situation, and
   $Y_1$ and $Y_2$ are points on the first or second reference curves in the spontaneous rhythm situation.

7. The device of claim 1, the operations further comprising:
   applying, by the one or more electrodes, a stimulation with a short atrioventricular delay and a pacing rate above a spontaneous sinus rate to obtain a first series of cardiac cycles in a situation of complete capture; and
   identifying a representative cardiac cycle from the first series of cardiac cycles for generating the first reference curve.

8. The device of claim 1, wherein the at least one descriptive parameter is a first descriptive parameter, the operations further comprising:
   comparing the first reference curve with the second reference curve to derive a second descriptive parameter representative of a similarity between the first reference curve and the second reference curve; and
   selectively utilizing the first reference curve and the second reference curve based on a determination that the second descriptive parameter satisfies a predetermined validation criterion.

9. The device of claim 1, the operations further comprising:
   applying, by the one or more electrodes, a stimulation with a long atrioventricular delay and a pacing rate above a spontaneous sinus rate to obtain a first series of cardiac cycles in a situation of spontaneous ventricular rhythm; and
   identifying a first representative cardiac cycle from the first series of cardiac cycles for generating the second reference curve.

10. The device of claim 9, wherein the stimulation is a first stimulation, the operations further comprising:
   applying, by the one or more electrodes, a second stimulation with a long atrioventricular delay and a pacing rate below the spontaneous sinus rate to obtain a second series of cardiac cycles for a situation of both atrial and ventricular spontaneous depolarization;
   identifying a second representative cardiac cycle from the second series of cardiac cycles for generating a third reference curve; and
   determining an offset value between a stimulated atrial event and a spontaneous atrial event based on the second reference curve and the third reference curve.

11. A method for quantifying a fusion rate, the method comprising:
   capturing, by one or more electrodes of an implantable medical device, at least two endocardial electrogram (EGM) signals during a first cardiac cycle;
   deriving, from the at least two EGM signals, at least two distinct temporal components;
   combining the at least two temporal components to generate a first parametric curve representative of the first cardiac cycle; and
   comparing the first parametric curve with a first reference curve corresponding to a complete capture situation to generate a first value for at least one descriptive parameter;
   comparing the first parametric curve with a second reference curve corresponding to a ventricular spontaneous rhythm situation to generate a second value for the at least one descriptive parameter; and
   in response to an occurrence of a fusion situation, generating a metric that quantifies the fusion rate for the fusion situation based on the first value and the second value.

12. The method of claim 11, wherein the at least one descriptive parameter includes two different descriptive parameters defining a two-dimensional (2D) space, the first value and the second value represented by two respective points in the 2D space, and wherein the metric is calculated based on a distance between each of the two respective points and an origin of the 2D space.

13. The method of claim 12, wherein at least one of the two different descriptive parameters is a correlation coefficient between norms of respective velocity vectors of the first parametric curve, the first parametric curve, and the second parametric curve.

14. The method of claim 12, wherein at least one of the two different descriptive parameters is an average angle between the respective velocity vectors of the first parametric curve, the first parametric curve, and the second parametric curve.

15. The method of claim 11, wherein the fusion rate is expressed in terms of a percentage of complete capture, the percentage of capture calculated as $$50 + \left(50 \times \frac{(A_2 - A_1)}{(X_2 - X_1)}\right)$$

for situations in which the first cardiac cycle is closer to a complete capture than to a spontaneous rhythm and as $$50 - \left(50 \times \frac{(B_1 - B_2)}{(Y_1 - Y_2)}\right)$$

for situations in which the first cardiac cycle is closer to the spontaneous rhythm than to the complete capture, wherein:
- $A_1$ and $A_2$ are points on the first parametric curve in situations where the first cardiac cycle is closer to a complete capture than to a spontaneous rhythm,
- $B_1$ and $B_2$ are points on the first parametric curve in situations where the first cardiac cycle is closer to the spontaneous rhythm than to the complete capture,
- $X_1$ and $X_2$ are points on the first or second reference curves in the complete capture situation, and
- $Y_1$ and $Y_2$ are points on the first or second reference curves in the spontaneous rhythm situation.

16. The method of claim 11, further comprising:
applying, by the one or more electrodes, a stimulation with a short atrioventricular delay and a pacing rate above a spontaneous sinus rate to obtain a first series of cardiac cycles in a situation of complete capture; and
identifying a representative cardiac cycle from the first series of cardiac cycles for generating the first reference curve.

17. The method of claim 11, wherein the at least one descriptive parameter is a first descriptive parameter, the method further comprising:
comparing the first reference curve with the second reference curve to derive a second descriptive parameter representative of a similarity between the first reference curve and the second reference curve; and
selectively utilizing the first reference curve and the second reference curve based on a determination that the second descriptive parameter satisfies a predetermined validation criterion.

18. The method of claim 11, further comprising:
applying, by the one or more electrodes, a stimulation with a long atrioventricular delay and a pacing rate above a spontaneous sinus rate to obtain a first series of cardiac cycles in a situation of spontaneous ventricular rhythm; and
identifying a first representative cardiac cycle from the first series of cardiac cycles for generating the second reference curve.

19. The method of claim 18, wherein the stimulation is a first stimulation, the method further comprising:
applying, by the one or more electrodes, a second stimulation with a long atrioventricular delay and a pacing rate below the spontaneous sinus rate to obtain a second series of cardiac cycles for a situation of both atrial and ventricular spontaneous depolarization;
identifying a second representative cardiac cycle from the second series of cardiac cycles for generating a third reference curve; and
determining an offset value between a stimulated atrial event and a spontaneous atrial event based on the second reference curve and the third reference curve.

20. A non-transitory computer-readable medium comprising instructions stored thereon that, when executed by a processor of an active implantable medical device, cause the processor to:
capture, by one or more electrodes of the active implantable medical device, at least two endocardial electrogram (EGM) signals during a first cardiac cycle;
derive, from the at least two EGM signals, at least two distinct temporal components;
combine the at least two temporal components to generate a first parametric curve representative of the first cardiac cycle; and
compare the first parametric curve with a first reference curve corresponding to a complete capture situation to generate a first value for at least one descriptive parameter;
compare the first parametric curve with a second reference curve corresponding to a ventricular spontaneous rhythm situation to generate a second value for the at least one descriptive parameter; and
in response to an occurrence of a fusion situation, generate a metric that quantifies a fusion rate for the fusion situation based on the first value and the second value.

* * * * *